United States Patent [19]
Lindegren

[11] Patent Number: 6,129,747
[45] Date of Patent: Oct. 10, 2000

[54] CONNECTOR ASSEMBLY FOR PRODUCING A MULTIPOLAR PIN CONNECTION BETWEEN AN ELECTRODE CABLE AND AN IMPLANTABLE MEDICAL DEVICE

[75] Inventor: Ulf Lindegren, Enskede, Sweden

[73] Assignee: Pacesetter AB, Järfälla, Sweden

[21] Appl. No.: 09/214,083

[22] PCT Filed: Jun. 5, 1997

[86] PCT No.: PCT/SE97/00985

§ 371 Date: Dec. 21, 1998

§ 102(e) Date: Dec. 21, 1998

[87] PCT Pub. No.: WO97/49456

PCT Pub. Date: Dec. 31, 1997

[30] Foreign Application Priority Data

Jun. 27, 1996 [SE] Sweden ................................. 9602547

[51] Int. Cl.$^7$ ...................................................... A61N 1/36
[52] U.S. Cl. ............................................................. 607/37
[58] Field of Search ......................... 607/36, 37; 439/909

[56] References Cited

U.S. PATENT DOCUMENTS 4,774,951 10/1988 Osypka ....................................... 607/37
4,934,366 6/1990 Truex et al. .
5,336,246 8/1994 Dantanarayana .

Primary Examiner—Scott M. Getzow
Attorney, Agent, or Firm—Hill & Simpson

[57] ABSTRACT

A connector assembly for an implantable medical device such as a heart stimulator having a hermetically sealed enclosure containing electrical circuits and a power source, is affixed to the enclosure of the stimulator or is incorporated therein for producing an electrical connection between a proximal end of an electrical cable and the circuits in the enclosure. The connector assembly has a first connector in the form of a female connector part with the electrical contacts embedded in a puncturable membrane disposed inside of the connector assembly. The first connector is placed in electrical contact with a second connector which is arranged on a male connector part on the proximal end of the electrode cable. The second connector is equipped with two or more contact needles pointing in the same direction, with respective tips which are insertable into the membrane so that as the tips puncture the membrane, they come into contact with respective electrical contacts of the first connector embedded in the membrane.

10 Claims, 2 Drawing Sheets

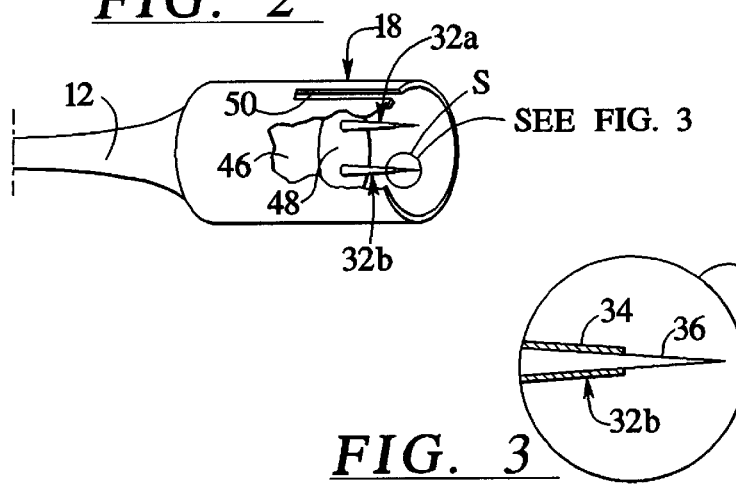
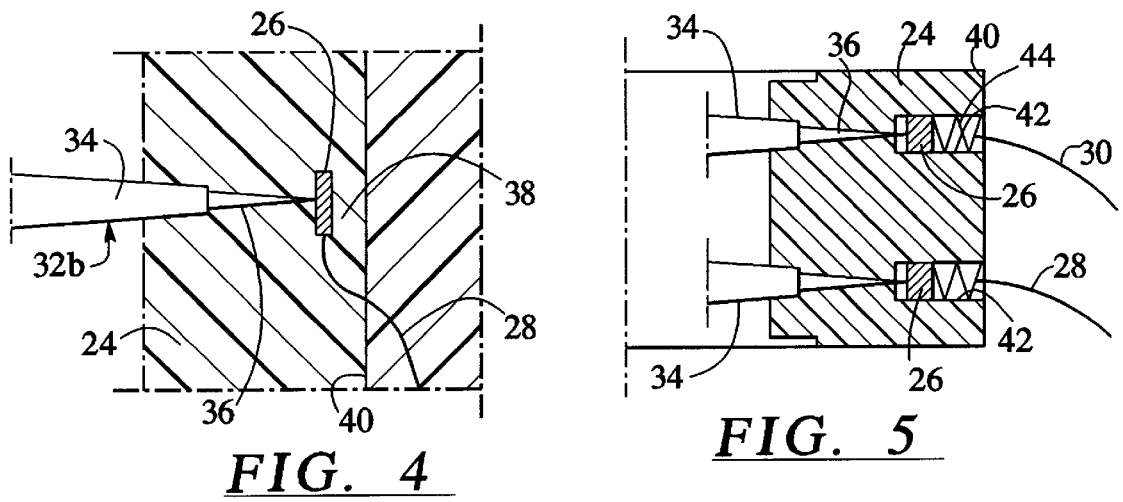
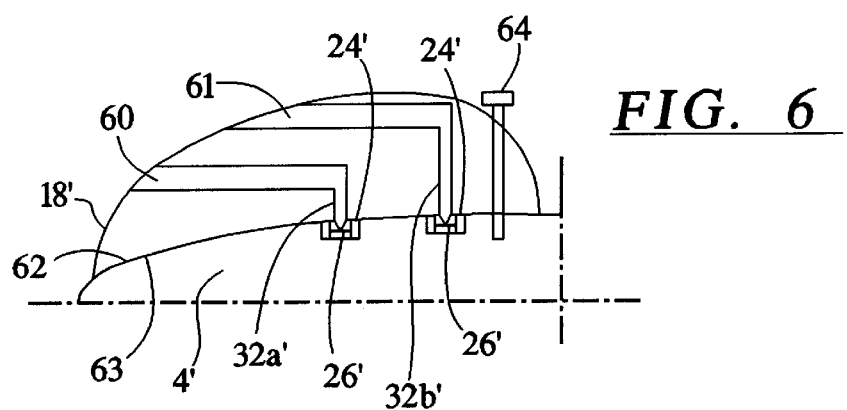

CONNECTOR ASSEMBLY FOR PRODUCING A MULTIPOLAR PIN CONNECTION BETWEEN AN ELECTRODE CABLE AND AN IMPLANTABLE MEDICAL DEVICE

BACKGROUND OF THE INVENTION

1. Field of the Invention

The present invention relates to a connector assembly for an implantable medical device, such as a heart stimulator. accordance with the preamble of the appended independent claims.

2. Description of the Prior Art

U.S. Pat. No. 4,934,366 discloses an implantable medical device in the form of a heart stimulator (pacemaker) in a hermetically sealed enclosure containing electrical circuits, a battery connected to the circuits and a connector part through which the proximal end of an electrode cable can be connected to the heart stimulator and electrically coupled to its circuits. The connector part comprises a tubular sleeve devised as a female connector part with a stepped, cylindrical receptacle, closed at its inner end and open on the end opening onto the exterior of the enclosure, and a middle section between both these channel sections. The diameter of the channel is smallest in its innermost section, largest in its outermost section and intermediate in size in its middle section.

A first, ring-shaped coil spring contact means is disposed in the wall of the inner part of the receptacle channel, and a second ring-shaped coil spring contact means is in the wall of the middle section. Both these contact means are electrically connected to the pacemaker's electrical circuits.

A connector, devised as a male connector with an anterior, narrow, pin-like tip electrode and a ring-electrode, arranged somewhat behind same and with a larger diameter than the diameter of the tip electrode, is devised to interact with the device's tubular female connector. When the male connector is inserted into the female connector, the tip electrode and the ring electrode are brought into electrical contact with the respective coil spring contact means in the tubular connector.

The tip electrode, devised as a cylindrical male connector, is axially separated from the ring electrode by a cylindrical spacer made of an electrically non-conductive material. The receptacle of the tubular connector, devised as a female connector, is also equipped with circular ring seals in the inside walls of the receptacle. These seals are intended to keep the two electrodes of the male connector from coming into electrical contact with each other via body fluid which could seep in through the gap between the exterior of the male connector and the interior of the female connector. The exterior of the male connector behind the ring electrode, which has the greatest diameter, also has encircling, external sealing ribs to seal against the interior of the female connector, thereby preventing the entry of fluid into the aforementioned gap.

Devising the electrically non-conductive spacer section between the tip electrode and a ring electrode at the proximal end of an electrode cable with external, encircling sealing ribs with intermediate grooves is also known.

The device according to U.S. Pat. No. 4,934,366 relates to bipolar connection of an electrode cable to the device's connector part. Since the contact means/electrodes of the interconnectable male and female connector parts therein are axially separated by intermediate spacer sections, a connector is achieved with a relatively great axial length. This length is obviously a disadvantage, since the aim is always to achieve the smallest possible external dimensions for an implantable device of the present kind.

With regard to heart stimulators, the trend is to stimulate the heart using more than two electrodes, implantable in the heart, on the electrode cable. Modification of the aforementioned known type of axial, bipolar electrode connection to accomodate e.g. three or more electrodes should result in an even longer connector part, since more than two coaxial electrodes must then be arranged in axially separate locations with intermediate spacers. The need for effective sealing means (e.g. sealing ribs) to separate the electrodes (i.e. the poles) from each other in the connector at the proximal end of the electrode cable increases to a corresponding degree. Therefore multipolar electrode connection increases both the size and constructional complexity of the sealing means employed to separate the poles from one another.

SUMMARY OF THE INVENTION

One object of the present invention is therefore to provide a connector assembly for an implantable medical device suitable for multipolar electrode connection. The connector assembly of the implantable device is either permanently affixed (e.g. molded-on) to the device's enclosure or built-into or affixable to the device's enclosure.

A second object of the invention is to provide a connector assembly for a medical device, suitable for multipolar electrode cable connection, in which the axial length of the connecting parts is independent of the number of connecting electrodes (poles) in the contact on the electrode cable's proximal end.

A third object of the invention is to provide a connector assembly for an implantable medical device in having a single, shared sealing means to separate and insulate the male connector part's poles from each other.

The above objects are achieved according to the invention in a connector assembly having a first connector, devised as a female connector part with an electircal contact means, embedded in a puncturable membrane, is arranged in the enclosure, the first connector being devised to be brought into electrical contact with a second, connector part, devised as a male connector part, on the proximal end of the electrode cable. This second connector is equipped with at least one contact needle, with a tip insertable into the membrane, which is brought into contact with the associated an electircal contact in the membrane of the first connector when the connectors are coupled. Each contact needle can be appropriately enclosed in insulation except in the area of the outermost part of the needle tip.

The membrane is self-sealing, i.e. the membrane will resiliently and sealingly enclose the tips of the contact needles when the needles are inserted in the membrane. The opening made by the needle will also close if the needle is withdrawn.

The first connector, devised as a female connector part, may appropriately be permanently mounted at the bottom hole end of an oblong receptacle provided in the connector, the second connector and the walls of the receptacle being provided with interacting position-fixation means preventing undesirable rotation of the second connector in the receptacle and ensuring the desired axial orientation and interaction of the associated electrical contact connector needles. The male connector part may be a DIN-type connector part. In this embodiment the connector part is designed as a part permanently affixed (e.g. molded-on) to the device's enclosure or built-into the device's enclosure.

In another embodiment the female connecting part may be provided directly in a surface contact part of the enclosure and the male part may be designed as a connector part having a contact surface which is contoured to conform with the enclosure contact surface. A separate attaching elements, for instance in the form of an attachment screw, can be provided for attaching the connector part to the enclosure.

The electrical contact in the first connector's membrane is preferably one or more metallic contact plates, elastically arranged (suspended and/or supported) in the connector and electrically connected to circuits in the enclosure by separate conductors in the connector part.

In one embodiment of the device, the metallic contact plates are embedded in the membrane made of an electrically insulating elastic material, such as rubber or plastic. Alternatively, the metallic contact plates could be movingly arranged inside open recesses in the membrane, on the side facing the connecting part, pressure springs, which pretension the contact plates, being mounted in the recesses between the plates and the said bottom of this recess. The membrane is preferably made of an electrically insulating, elastic material, such as rubber or plastic.

The second connector preferably has a basic body of electrically insulating material holding the connector's contact pins, and this basic body has an end surface from which the projecting parts, formed by the contact needles, of the contact pins, are parallel to each other, i.e. side by side.

DESCRIPTION OF THE DRAWINGS

The invention will now be further described and explained with the embodiments, schematically depicted in the attached drawings, showing how the connecting part of an implantable heart stimulator (pacemaker) and the connecting part on the proximal end of its associated electrode cable can be devised in achieving the invention. The drawings are only intended to elucidate the principle of the construction of the invention and do not claim to show the invention with dimensional accuracy or to scale.

FIG. 2 is a perspective view, on a larger scale, of a partially sectioned connector on the proximal end of the electrode cable.

FIG. 3 shows, on an even larger scale, the end area of a connector's contact pins inside the circle S in FIG. 2.

FIG. 4 shows a section through the membrane at the bottom hole end of the heart stimulator's connector receptacle according to FIG. 1.

FIG. 5 show a section, corresponding to the section in FIG. 4, through a membrane at the bottom hole end of the connector receptacle.

FIG. 6 illustrates schematically another embodiment of the invention in which the connector on the proximal end of the electrode cable is designed as a connector part to be attached against the housing.

DESCRIPTION OF THE PREFERRED EMBODIMENTS

Figure 1:
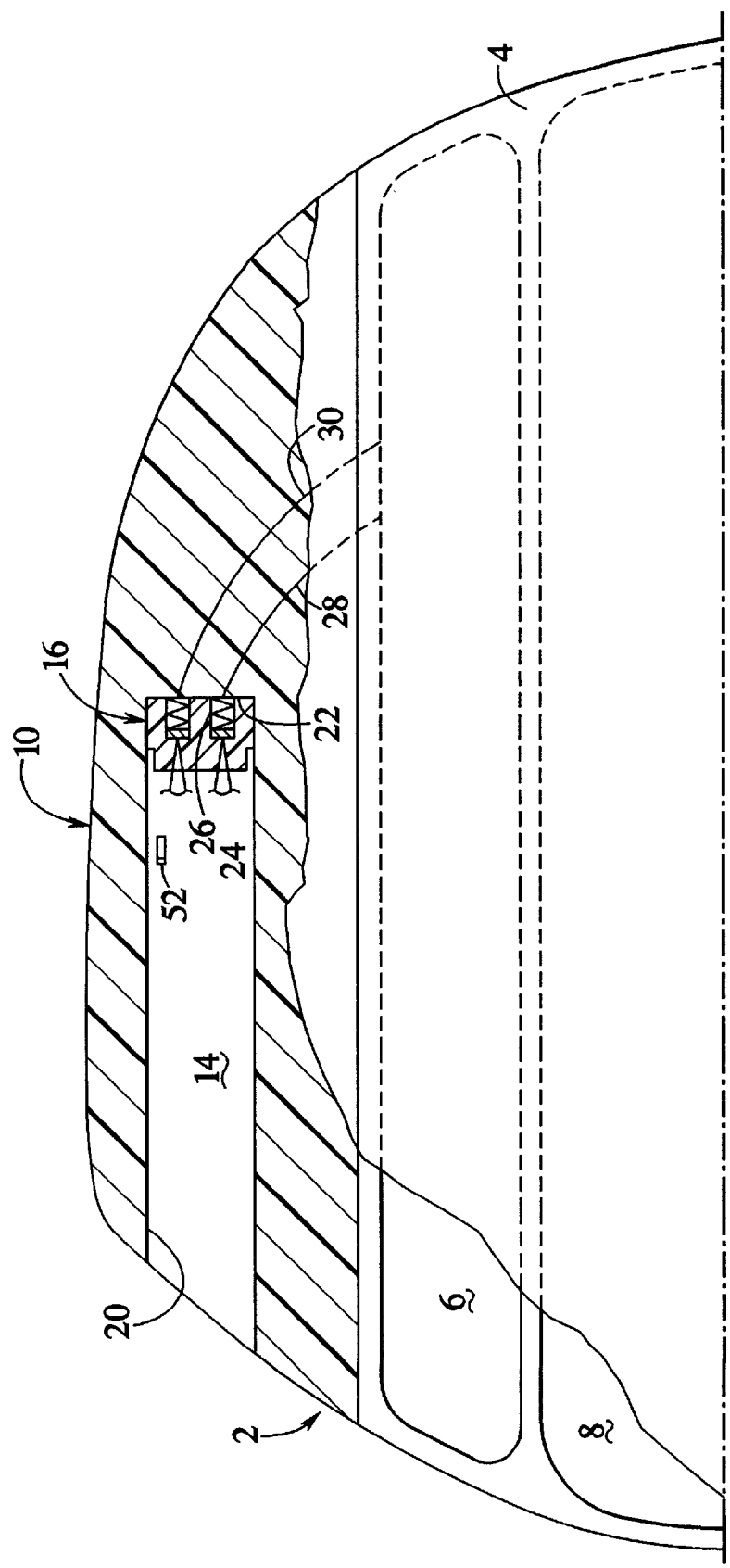
FIG. 1 shows, in a lateral, partially sectioned view, a first embodiment of the connector area of a heart stimulator with relevant parts of a connected connector on the proximal end of an associated electrode cable (not shown).

Referring first to FIG. 1 which, in a lateral, partially sectioned view shows the upper part of a heart stimulator or pacemaker generally designated 2. In the customary manner, the heart stimulator has a hermetically sealed enclosure 4 containing electrical circuits 6 and a power source 8, e.g. in the form of a battery. Near or in the upper part of the enclosure 4, a connector assambly 10 is arranged for electrical connection of the proximal end of an electrode cable 12 (cf FIG. 2) to the circuits 6 in the enclosure 4. The connector assembly 10 has an oblong receptacle 14, intended for receiving a first connector 16 into the connector part and a second connector 18 on the electrode cable's proximal end 12 (cf FIG. 2) which can be inserted into the receptacle 14 for coupling with the connector 16. The preferably cylindrical receptacle 14 has an input end 20, opening onto the exterior of the connecting part, and a bottom hole end 22 inside the connecting part 10. The first connector 16, devised as a female connector part, is therefore arranged at the bottom hole end 22 of the receptacle 14. The connector 16 includes a puncturable membrane 24 made of an elastic, electrically insulating material, such as rubber or plastic. Two or more electrical contacts 26, depending on whether the connector 16 is bipolar or multipolar, are enclosed in this membrane 24. The number of electrical contacts 26 in the connector 16 obviously depends on whether the connector on the distal end (not shown) of the electrode cable 12 has two or more active electrodes, i.e. whether it is bipolar or multipolar. For the sake of simplicity, the connector 16 in FIG. 1 is shown as a bipolar connector, i.e. a connector with only two separate electrical contacts 26. The connector 16 shown in FIG. 1 could also be devised as a quadripolar connector, only two of the electrical contacts 26 being shown in FIG. 1. The electrical contacts 26 in the connector's 16 membrane 24 are metallic contact plates which are elastically arranged in the membrane 24 in the connector assembly 10 and which are electrically connected to the circuits 6 in the enclosure 4 by separate electrical conductors 28 and 30 respectively in the connector part.

The first connector 16, arranged as a female connector part in the connector assembly 10, is therefore designed for electrical coupling to the second connector 18, devised as a male connector part, on the proximal end of the electrode cable 12 when inserted into the receptacle 14 and for coupling to the connector 16. The second connector 18 (cf FIG. 2) is a DIN-type connector, i.e. it consists of a sleeve-like, hollow, cylindrical connector with two or more parallel contact needles or contact pins 32a, 32b, . . . . If the connector 18 is e.g. a multipolar connector with four, five or more contact pins 32, the pins are appropriately arrayed in a ring around the cylindrical connector's 18 imaginary central axis in the known manner. As the enlargement in FIG. 3 shows, contact needles or pins 32 can be inserted without difficulty into the elastic membrane 24.

As FIGS. 3 and 4 show, each contact needle 32 is provided with surrounding insulation 34, except in the area of the outermost part 36 of the needle tip which is intended to be brought into electrical contact with an associated contact element 26 in the membrane 24. The main purpose of the insulation 34 is to keep the metallic contact needle from coming into contact with the body fluid which could invade the receptacle 14 after the heart stimulator 2 has been implanted into the body. As an alternative to providing the contact needles or pins 32 with such insulation, the interior of the receptacle 14 could be equipped, at appropriate sites and/or on the exterior of the connector 18, with appropriate sealing means which keep body fluid from invading the space between the connector's free, anterior end surface and the opposing frontal surface of the connector 16, i.e. the frontal surface of the membrane 24.

Thus, the membrane 24 serves as a common sealing means for all the contact pins, thereby achieving both sealing and insulation between the non-insulated end sections 36 of the needles. The length of the contact needles 32 could e.g. be about 5 mm, and the length of the non-insulated end section 36 must obviously be less than the membrane's 24 thickness, which e.g. could be about 3 mm. The length of the end section 36 can be very small, e.g. 0.1 mm.

Each electrical contact 26 devised as metallic contact plates can be completely embedded in the membrane 24, whereby membrane material in the area 38 between the electrical contact means 26 and the receptacle's 14 bottom 40 of the receptacle 14 serves as an elastic shim when each electrical contact means 26 establishes contact with the sharp-tipped end section 36 of the respective contact needle, thereby being pressed towards the bottom 40. However, the elastic inclusion of electrical contacts 26 in the membrane 24 can be achieved in many different ways, one being shown in FIG. 5. In this instance, electrical contacts 26 devised as metallic contact plates are movably arranged inside respectively open recesses or holes 42 in the membrane 24, on the side facing the bottom 40 of the receptacle 14. In this instance, pressure springs 44, exerting a pre-tensioned force on the electrical contacts 26 towards the non-insulated end sections or tips 36 of the contact needles, are arranged between the plates 26 and the bottom 40.

The second connector 18 has a basic body 46, made of an electrically insulating material, which holds a connector's contact pin 32. The sharp-tipped contact needle's 32, projecting from the free end surface 48 of this basic body, are parallel to each other.

As the above shows, the first connector 16 is permanently arranged at the bottom hole end of the receptacle 14, and appropriately interacting position-fixing components, intended to prevent undesirable rotation of the second connector 18 in the receptacle 14, are provided on the second connector 18 at the proximal end of the electrode cable 12 and in the wall of the receptacle. The task of these position-fixation components is to achieve the desired positioning of the connector 18 when the latter is inserted into the receptacle 14, thereby ensuring the desired axial positioning and interaction of associated electrical contacts 26 and contact needles 32. These position-fixation components can e.g. be of a axial slot 50 in the wall of the connector 18 and a projection 52, mating with this slot, on the interior wall of the receptacle 14.

It should be noted that the second connector 18 does not necessarily have to be cylindrical but may have any suitable cross-section, for instance a cross-section which is square or rectangular. In this case the cross-sectional shape of the connector could serve as said a position-fixing (i.e., anti-rotation) arrangement in conjunction with an oblong receptacle having a complementary shape.

This DIN-type connector also has the advantages of a standard DIN-connector as used in audio applications in which for instance the female part would contain a set of contacts connected to both input and output means whereas the male part might only contain a smaller number of pin contacts for connection to the input means whilst still fitting the female contact. The male part in the DIN-type connection described above thus could contain fewer needle contacts contacting only a selection of the contacts in the female part which would correspond to a selection amongst the possible functions of the pacer.

FIG. 6 illustrates a variation of the above embodiment. In this embodiment a male connector part 18' is designed to be attached to the outside of the enclosure. The male connector part 18' preferably has the general configuration of a standard molded-on connector part with standard 3.2 mm female connection openings 60, 61 for standard lead connections such as any of the IS-1 or VS-1 standards. The connector part 18' may of course be provided with any kind of detachable lead connection, including the DIN-type connection described above. The leads may also be permanently attached to the connector part.

The contact surface 62 of the connector part 18' is contoured to conform with one part of the surface of the enclosure serving as the enclosure contact surface 63. This side of the connector part is provided with one or more contact needles 32a', 32b' extending from the surface and pointing in the same direction. The design of the needles may be any one of the designs described above in connection with the DIN-type connector.

The enclosure contact surface 63 is provided with electrical contacts 26' embedded in a puncturable membrane 24' arranged flush with the surface or slightly recessed therein. The design of these electrical contacts 26' and membranes 24 may be any one of the designs described above in connection with the DIN-type connector.

The connector part 18' may be provided with position-fixation means. These means may for instance be in the form of a peripheral groove on the male connector part cooperating with a corresponding flange on the enclosure or vice versa. The groove further could contain a sealing means in the form of a flexible sealing bead pressed into the groove. Of course any cooperating components which prevents rotation by means of mutual, complementary shapes could be used. The position-fixation components cooperate with an attachment components which may be in the form of one or more screws 64 which can be screwed into a threaded bore in the enclosure.

As in the case of the DIN-type connector described above, the number of the electrical contacts may be adapted to the number of different functions the pacemaker may have, the number and location of the contact needles either being adapted to the locations of all electrical contacts or being adapted to the number and locations of electrical contacts corresponding to a selection of the functions it is desired to utilize in a particular case.

As indicated above, normally a contact block made of transparent epoxi resin is molded against the enclosure, the female contact means for the proximal end of the lead being molded into the contact block at the same time that the block is molded against the enclosure. This procedure is complicated and time-consuming, one reason being that the curing of the epoxi resin after the molding of the block onto the enclosure takes time.

This second embodiment with a connecting part in the shape of a molded-on part thus has the advantage that the connecting part and the enclosure can be manufactured separately and independently under the most favorable conditions for the respective component. Given that the enclosure has several female contacts corresponding to a number of different functions, it will be easy to manufacture pacers with different functions without essentially altering the enclosure and its contents since the locations and numbers of the male contacts in the block freely can be chosen to give a specific selection of functions. The block can be attached to the enclosure either at the manufacture or possibly in connection with the implantation of the device.

Although modifications and changes may be suggested by those skilled in the art, it is the intention of the inventor to embody within the patent warranted hereon all changes and modifications as reasonably and properly come within the scope of his contribution to the art.

I claim as my invention:

1. A connector assembly for an implantable medical device, said connector assembly comprising:

a female connector housing having a receptacle therein and including a puncturable, self-sealing membrane in said receptacle and an electrically conductive electrical contact disposed relative to said membrane so as to be accessible by puncturing said membrane; and a male connector insertable into said receptacle, adapted for mechanical and electrical connection to an electrode cable, including an electrically conductive contact needle for producing an electrical connection with said electrical contact by puncturing said membrane when said male connector is fully inserted in said receptacle.

2. A connector assembly as claimed in claim 1 wherein said receptacle is an oblong receptacle having an open entry end, and a bottom end disposed inside said housing, said puncturable membrane forming said bottom end of said receptacle and said contact elements being embedded in said puncturable membrane.

3. A connector assembly as claimed in claim 2 wherein said male connector comprises a DIN-type connector carrying said contact needle.

4. A connector assembly as claimed in claim 1 wherein said enclosure has a surface and wherein said contact element is disposed on said surface of said enclosure, and wherein said contact assembly further comprises a housing containing said male connector having a housing surface conforming to said surface of said enclosure, said contact needle extending through said housing to said surface of said enclosure.

5. A connector assembly as claimed in claim 1 wherein said contact element comprises a resiliently mounted metal plate having a separate electrical conductor.

6. A connector assembly as claimed in claim 5 wherein said metal contact plate is embedded in said membrane, and wherein said membrane is comprised of an electrically insulating, elastic material.

7. A connector assembly as claimed in claim 5 wherein said membrane has a recess therein with an open end and a bottom end, said bottom end being puncturable by said male connector, said metal contact plate being disposed in said receptacle with a first side facing said bottom end and a second side facing away from said bottom end, and said female connector further comprising a pressure spring disposed in said receptacle at said second side of said contact plate for urging said contact plate toward said bottom end.

8. A connector assembly as claimed in claim 1 wherein said membrane is comprised of an electrically insulating, elastic material.

9. A connector assembly as claimed in claim 1 wherein said receptacle has a receptacle wall interacting with said male connector to prevent rotation of said male connector in said receptacle.

10. A connector assembly as claimed in claim 1 further comprising a first position-fixing component disposed in said receptacle and a second position-fixing component carried by said male connector, said first position-fixing component and said second position-fixing component interacting with each other to prevent rotation of said male connector in said receptacle relative to said female connector housing.

* * * * *